United States Patent [19]
Berndtsson et al.

[11] Patent Number: 6,098,471
[45] Date of Patent: Aug. 8, 2000

[54] DILUTING AND MEASURING DEVICE FOR PARTICLE COUNTING

[75] Inventors: Ingemar Berndtsson, Sollentuna; Tommy Andersson, Vällingby; Abraham Bottema, Sorunda, all of Sweden

[73] Assignee: Boule Medical AB, Stockholm, Sweden

[21] Appl. No.: 09/091,345

[22] PCT Filed: Nov. 17, 1997

[86] PCT No.: PCT/SE97/01923

§ 371 Date: Jun. 17, 1998

§ 102(e) Date: Jun. 17, 1998

[87] PCT Pub. No.: WO98/22797

PCT Pub. Date: May 28, 1998

[30] Foreign Application Priority Data

Nov. 20, 1996 [SE] Sweden .................................. 9604259

[51] Int. Cl.[7] ............................. G01N 15/10; G01N 1/38
[52] U.S. Cl. ................. 73/864.87; 73/61.71; 73/864.21; 73/864.22
[58] Field of Search ............................. 73/865.5, 864.21, 73/864.22, 864.81, 864.83–64.87, 61.71

[56] References Cited

U.S. PATENT DOCUMENTS

| | | | |
|---|---|---|---|
| 3,165,693 | 1/1965 | Isreeli et al. ............................ | 324/71.1 |
| 3,496,970 | 2/1970 | Pontigny ................................ | 141/105 |
| 4,090,129 | 5/1978 | Gear ....................................... | 324/71.1 |
| 4,607,526 | 8/1986 | Bachenheimer et al. ........ | 73/864.81 X |
| 5,007,296 | 4/1991 | Hukuhara ............................. | 73/864.87 |
| 5,589,394 | 12/1996 | Kim et al. ................................ | 436/63 |
| 5,812,419 | 9/1998 | Chupp et al. ............................ | 702/21 |
| 5,882,599 | 3/1999 | Gilbert ................................... | 422/100 |

OTHER PUBLICATIONS

Abstract of SE 456866 B inventor Berntsson pub. Nov. 7, 1988 abstract by Derwent Information LTD acc. No. 1988–336150 entitled Appts. for volume determn. dilution and transmission of liq. specimens.

*Primary Examiner*—Thomas P. Noland

[57] ABSTRACT

A device for particle counting includes a metering device for metering a volume of a liquid sample containing particles and a cylinder for dosing a volume of a diluting liquid to a dilution chamber. The cylinder has first and second ends and a piston. A conduit connects a first end of the cylinder and the dilution chamber. The metering device introduces the liquid sample in the conduit and movement of the piston towards the first end displaces diluting liquid and sample to the dilution chamber which communicates with the second end of the cylinder and is preferably located therein, whereby movement of the piston towards the second end causes pressurizing of the dilution chamber to displace diluted sample from the dilution chamber through a particle counter. The piston has a piston rod extending through the first cylinder end, whereby movement of the piston towards the first end causes an increase in volume ($V_2$) in the cylinder on the second piston side that is greater than the decrease in volume ($V_1$) in the cylinder on the first piston side. The increase causes a lowered pressure on the second piston side that draws air into the dilution chamber.

11 Claims, 5 Drawing Sheets

PRIOR ART

DILUTING AND MEASURING DEVICE FOR PARTICLE COUNTING

CROSS-REFERENCES TO RELATED APPLICATIONS

This application is the national phase under 35 U.S.C. §371 of prior PCT International Application No. PCT/SE97/01923 which has an International filing date of Nov. 17, 1997 which designated the United States of America, the entire contents of which are hereby incorporated by reference.

BACKGROUND OF THE INVENTION

1. Field of the Invention

The present invention concerns a diluting and measuring device for particle counting. This device is particularly, but not exclusively, intended for the counting of blood cells.

2. Description of Related Art

It is known in the state of the art to count blood cells by causing an accurately defined volume of diluted blood sample to pass a so-called capillary, i.e., an extremely small hole, generally in a ruby, the hole having a diameter considerably larger than the size of a blood cell, typically 80 $\mu$m. A voltage is applied over the capillary, and, when a blood cell passes through the hole, the electrical resistance changes. This is because the cells can be regarded as insulators. Each change in resistance can be detected by suitable electronic equipment, and the sum of all changes detected corresponds to the number of blood cells having passed through the capillary. In order to obtain the concentration of cells in the original sample, the concentration of cells in the diluted sample is multiplied by the dilution factor, typically 1:40000 when counting of red blood cells (RBC) is concerned. It is obvious, that measuring of sample volumes and dilution liquid volumes must be performed in an accurate and repeatable way such that not only a correct degree of dilution can always be guaranteed but also a thorough and uniform mixing of the two volumes is ensured.

In a typical state of the art apparatus, a syringe is employed for providing a defined volume (typically 5 ml) of diluting liquid, and this volume is displaced through a conduit to a measuring chamber. On its way to the measuring chamber, the diluting liquid brings with it a defined volume (typically 25 $\mu$l) of blood sample previously introduced into the conduit. The blood sample mixes with and is diluted by the diluting liquid in the measuring chamber, which is, thus, also a dilution or mixing chamber, and a defined fraction of the diluted sample is further displaced through a capillary located in a wall of the measuring chamber, or, in a transducer located within the measuring chamber.

This state of art apparatus requires a syringe for the diluting liquid and a separate mixing/measuring chamber. It would be desirable, thus, to simplify the apparatus by combining the syringe and at least a mixing chamber.

Also, in this state of art apparatus, the mixing between the blood sample and the diluting liquid in the measuring chamber is caused by turbulence when the two liquids enter the measuring chamber and cannot be enhanced in any way. It would be desirable, thus, to enhance the turbulence in the mixing chamber, thereby to reach a more uniform mixing of the sample and the diluting liquid. One known method to achieve turbulence in a liquid is to let air bubbles into a mixing chamber at the bottom thereof by means of a pump. Evidently, the need of a pump makes the apparatus more expensive and cumbersome and increases the need of maintenance.

BRIEF SUMMARY OF THE INVENTION

The present invention has as its object to provide, on one hand, a possibility to combine a dosing syringe and a mixing chamber that may also be a measuring chamber, and on the other hand a means to enhance the mixing in a mixing chamber between a sample containing particles at a relatively high concentration and a diluting liquid by introducing air into the mixing chamber without the need for a pump or the like.

To achieve these objects, the present invention suggests, on one hand, to utilize the volumes of a syringe on either sides of its piston, on a first side for receiving and dispensing diluting liquid and on a second side for providing a mixing chamber that may be combined with a measuring chamber.

On the other hand, the present invention suggests introducing air at the bottom of the mixing chamber by lowering the pressure in the mixing chamber, so that air is sucked into the mixing chamber. Advantageously, a piston of the dosing syringe used for dosing the diluting liquid is also utilized for lowering the pressure in the mixing chamber. Preferably, the piston has a first side having a relatively small area for dosing the diluting liquid, and a second side having a relatively large area, so that a defined displacement of the piston in the dosing direction causes displacement of a defined volume of diluting liquid and an increase in volume on the second side of the piston that is greater than said defined volume. This, in turn, creates a lowered pressure in an air volume on the second side of the piston which is used to suck air into the mixing chamber.

BRIEF DESCRIPTION OF THE DRAWINGS

Embodiments of the present invention will be described hereinafter, reference being made to the annexed drawings, wherein.

DETAILED DESCRIPTION OF THE RELATED ART

Figure 1:
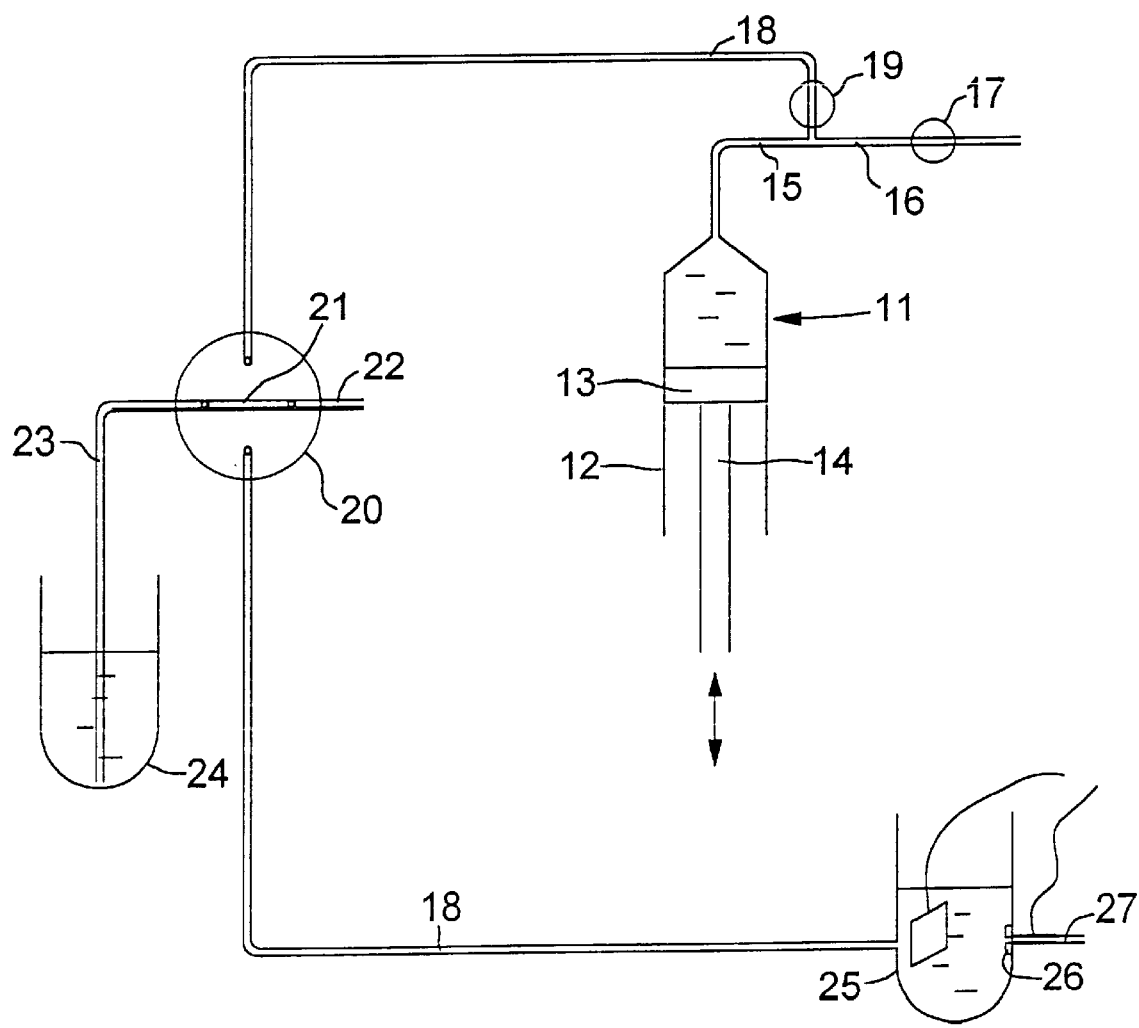
FIG. 1 is a schematic view showing a state of the art apparatus.

In the state of art arrangement according to FIG. 1, 11 is a syringe including a cylinder 12 and a piston 13 axially movable within the cylinder by means of a piston rod 14 extending through one end of the cylinder, that may be an open end. The opposite end of the cylinder is closed and connected to a conduit 15. This conduit 15 in turn communicates with a supply conduit 16 for diluting liquid having a valve 17 therein, and a discharge conduit 18 having a valve 19 therein. In the conduit 18 there is also a turning valve 20, the non-shown rotatable valve body of which has a through channel 21 and is positionable in two different positions. In a first position (shown in FIG. 1), the through channel communicates with a conduit 22 leading to a non-shown pump, and a conduit 23 communicating with a vessel 24 containing a blood sample to be diluted. The blood sample in the vessel 24 may be diluted already to a certain extent. The discharge conduit 18 ends in a mixing and measuring chamber 25. Upon operation of the pump, blood sample is transported from the vessel 24 through the valve 20 so as to fill the through channel 21. In a second position of the valve body, the through channel communicates with the conduit 18. Since the through channel 21 contains an accurately defined volume, turning of the valve body to the second position will put this defined volume in communication with the conduit 18.

The function of the known device is as follows: The valve 17 is opened and the piston lowered to suck a defined volume of diluting liquid into the syringe. Thereafter, the valve 17 is closed and the valve 19 opened, and the piston 13 is raised thereby displacing diluting liquid through the conduit 18 through the valve 20, the valve body of which being positioned in its second position so that the defined volume of blood sample is brought by the diluting liquid to the mixing and measuring chamber 25 where the very small volume of blood sample is to be mixed with and diluted by the relatively large volume of diluting liquid. In a wall of the chamber 25 there is a capillary 26 and a discharge conduit 27.

It is evident that the only mixing occurring in the chamber 20 is due to turbulence when the sample and the diluting liquid enter the chamber.

DETAILED DESCRIPTION OF THE INVENTION

To improve the mixing of the sample and the diluting liquid, the present invention provides for admission of air into the chamber without the need for a pump or the like.

Figure 2:
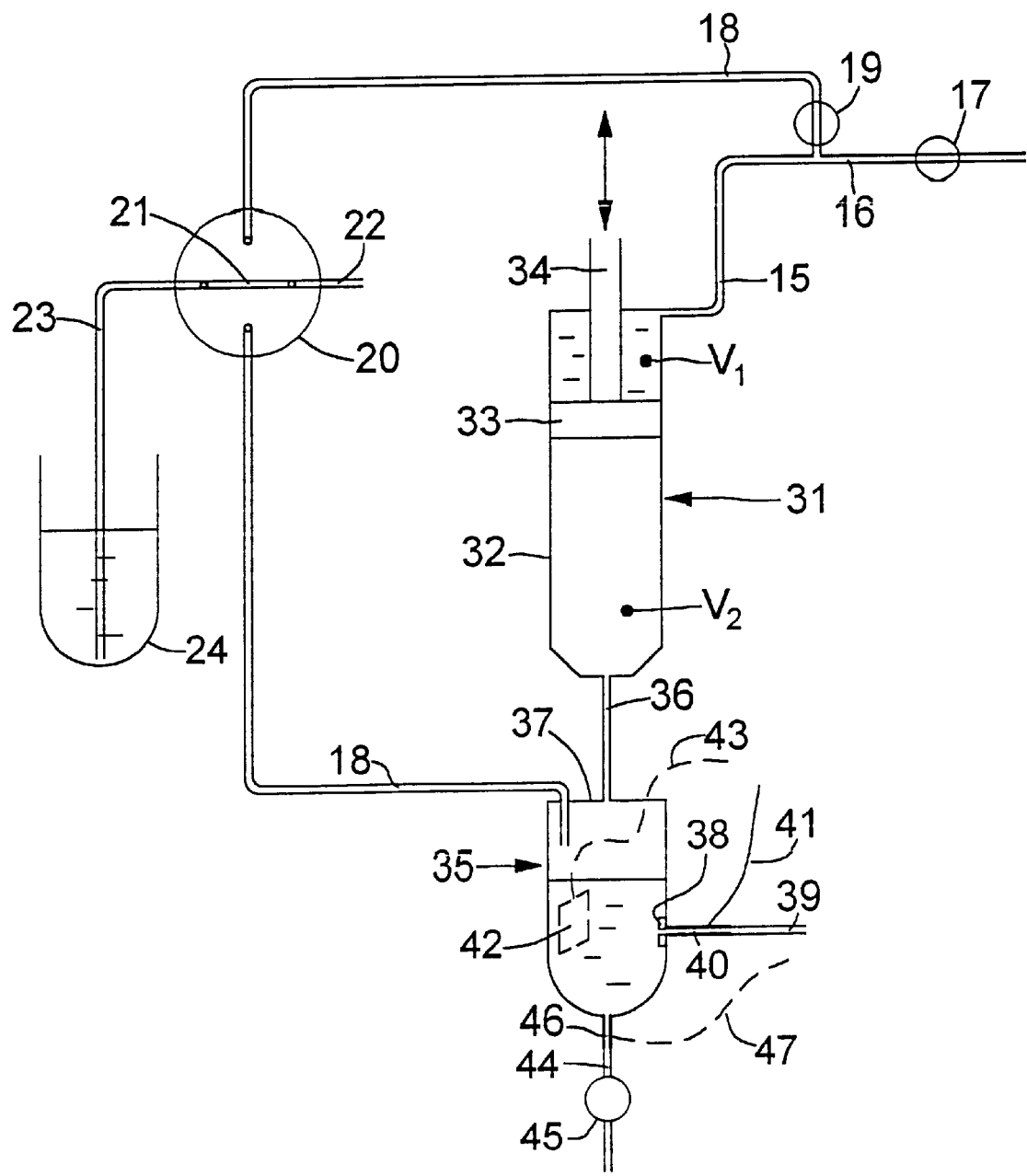
FIG. 2 is a schematic view showing a first embodiment of the present invention employing a combined mixing and measuring chamber separate from a syringe.

In FIG. 2, reference numerals 15–24 are used to designate items corresponding to those of FIG. 1. The syringe of FIG. 1 is replaced by a syringe 31 including a substantially vertical cylinder 32 having a double-acting piston 33 axially movable therein by means of a piston rod 34 attached to one side of the piston and sealingly extending through a closed end of the cylinder. The interior of this end of the cylinder communicates with the conduit 15. The opposite, lower end of the cylinder, which is likewise closed, communicates with a combined mixing and measuring chamber 35 through a conduit 36 opening in an upper closure 37. The discharge conduit 18 for diluting liquid extends through the closure and opens within the chamber 35. In a wall of the chamber is a capillary 38 and a discharge conduit 39 including a metallic portion 40 constituting an electrode connected to an electric wire 41. A further electrode 42 is located within the chamber 35 and is connected to an electric wire 43. At the bottom of the chamber 35 there is a conduit 44 having a valve 45. Also the conduit 44 may have a metallic portion 46 constituting an electrode connected to an electric wire 47. A voltage may be applied across the capillary by connecting wire 41 to one pole and either or both of wires 43, 47 to the other pole of a suitable electronic counting equipment.

The function of the apparatus of FIG. 2 is as follows: Valve 19 is closed and valve 17 opened and the piston rod 34 is operated to lower the piston a predetermined distance from its upper position. A diluting liquid, typically an isotonic solution of NaCl when dilution of a blood sample and counting of RBC is concerned, is drawn from a non-shown source into the upper volume $V_1$ of the syringe 31 through conduits 16 and 15. Thereafter, valve 17 is closed and valve 19 opened, and the valve body of turning valve 20 is rotated so as to connect its through channel 21 to conduit 18. Now the piston rod 34 is operated to raise the piston 33 thereby displacing the diluting liquid through conduits 15 and 18 and bringing along the blood sample from the through channel 21 to the chamber 35. Simultaneously, the lower volume $V_2$ of the syringe increases more than the upper volume $V_1$ decreases due to the larger effective piston area on the lower side of the piston. This leads to a lowering of the pressure in an air volume in the lower volume $V_2$. Now the valve 45 is opened and air under atmospheric pressure is allowed to enter the conduit 44 and the chamber 35 at its bottom to create at least one air bubble raising through the mixture of blood sample and diluting liquid therein creating further turbulence than was the result of the mere introduction of the sample with the diluting liquid. This results in the desired enhanced mixing and, as a consequence, a more uniform distribution of the blood cells within the volume.

Figure 3:
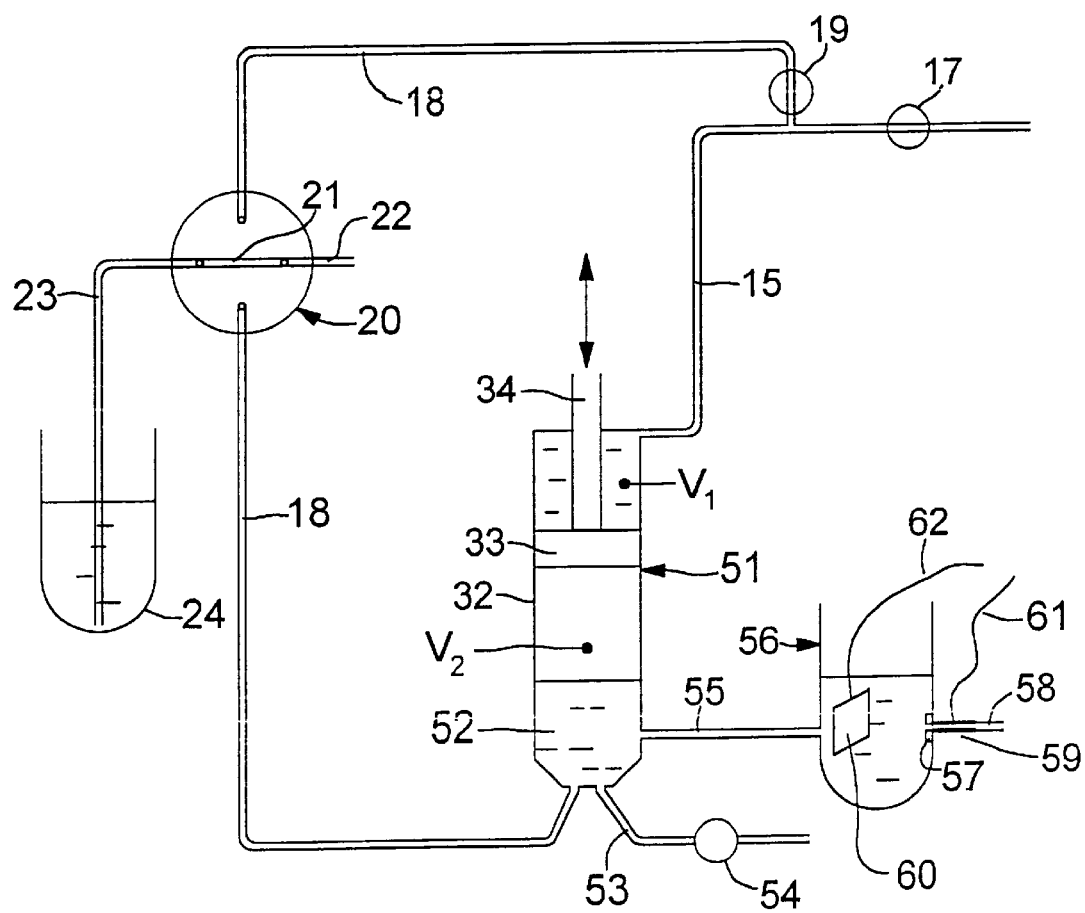
FIG. 3 is a schematic view showing a second embodiment of the present invention employing a mixing chamber integrated in a syringe and a separate measuring chamber.

The embodiment of FIG. 3 differs from that of FIG. 2 in that a mixing chamber is integrated in the syringe 51, simply by employing the lower volume $V_2$ as a mixing chamber 52 into which open the conduit 18 as well as an air inlet conduit 53 having a valve 54. A conduit 55 leads from the chamber 52 to a separate measuring chamber 56 having a capillary 57, a discharge conduit 58 as well as electrodes 59 and 60 with electric wires 61, 62, respectively. Whereas the entire lower volume $V_2$ was dry in the embodiment of FIG. 2, it will contain in FIG. 3 an upper air volume and a lower volume of blood sample and diluting liquid once the piston has been raised to displace the diluting liquid. As before, the differential in areas of the upper and lower sides of the piston causes lowering of the pressure in the lower volume $V_2$ which is used to draw air into the mixing chamber 52 upon opening of the valve 54.

Figure 4:
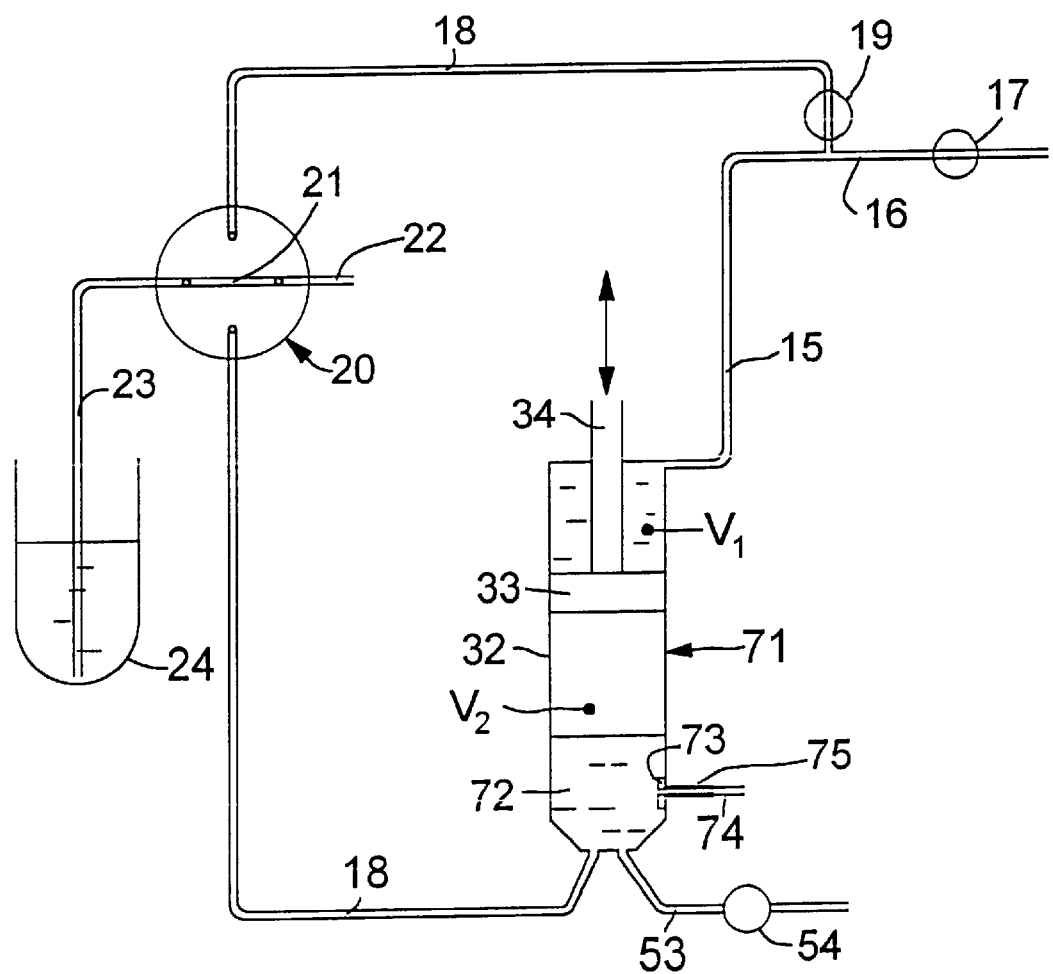
FIG. 4 is a schematic view showing a third embodiment of the present invention employing a combined mixing and measuring chamber integrated in a syringe.

The embodiment of FIG. 4 differs from that of FIG. 3 in that the syringe 71 employs its lower volume $V_2$ as a mixing and measuring chamber 72. Thus, the only difference in comparison to FIG. 3 is that a capillary 73 is located in the wall of the syringe and has a discharge conduit 74 with an electrode 75. At least one further electrode is arranged as a metallic portion of conduit 18 and/or conduit 53 (not shown).

Figure 5:
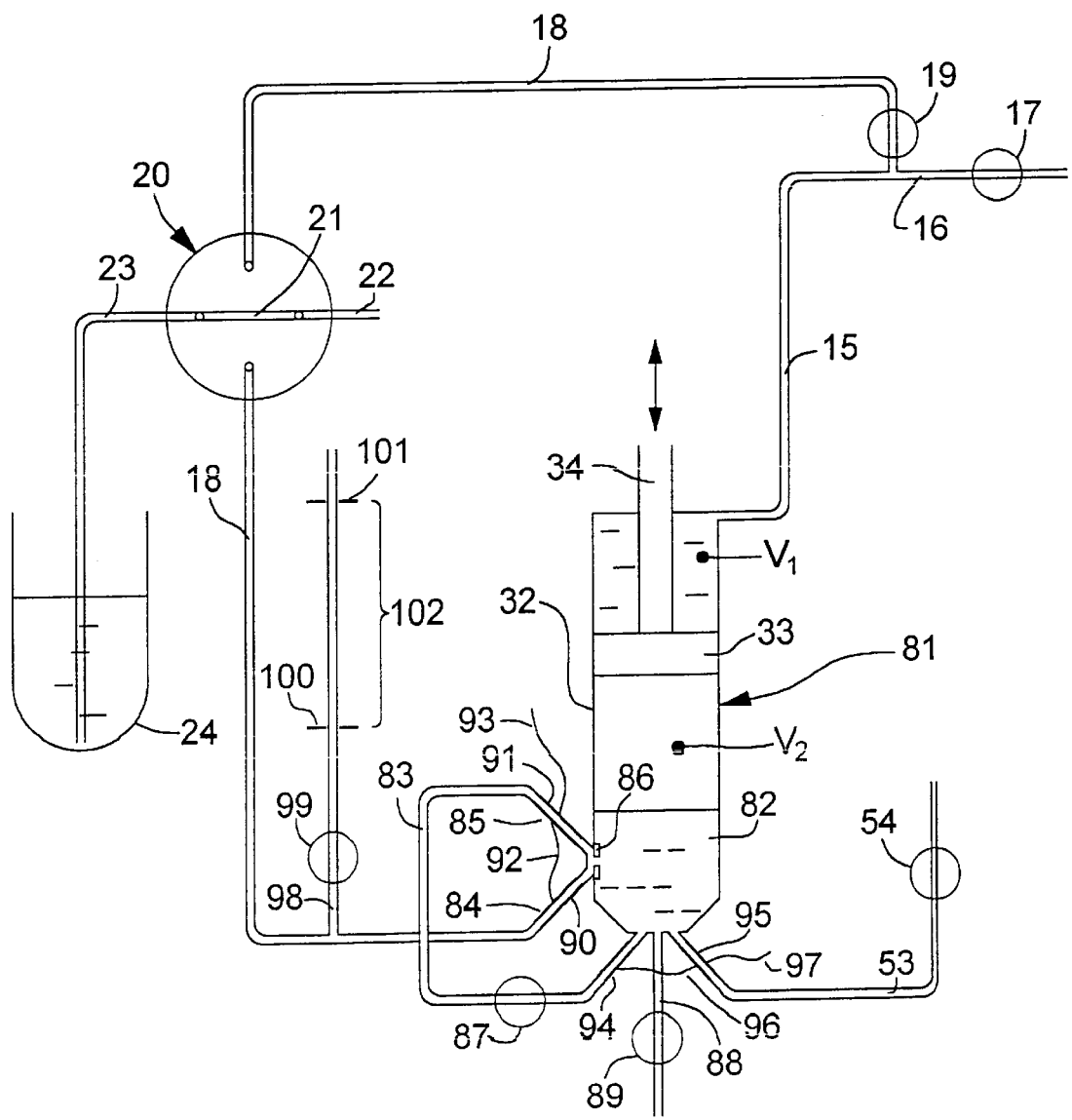
FIG. 5 is a schematic view showing a fourth, preferred embodiment of the present invention employing a combined mixing and measuring chamber integrated in a syringe.

FIG. 5 shows a preferred embodiment of a syringe 81 having a combined mixing and measuring chamber 82. Here, the conduit 18 for introduction of the sample and the diluting liquid into the chamber 82 describes a substantially vertical loop 83 before its end is connected to the bottom end of the syringe. The loop includes a V-shaped portion having a first leg 84 and a second leg 85. At the bottom of the V-shape the conduit 18 communicates with a capillary 86 located in the wall of the syringe. The conduit 18 has a further valve 87 between the loop and the syringe. At the bottom of the syringe there may be an emptying conduit 88 with a valve 89 (such conduit and valve may be provided on the syringes previously described as well). At least one electrode is provided on each side of the capillary, suitably by metallic portions of the conduits connected to the syringe. In order to reduce the influence of air bubbles possibly adhering to the inner sides of the conduits, it is preferred, however, that two electrodes are provided on each side. Thus, one electrode 90 is arranged on the leg 84 and one electrode 91 is arranged on the leg 85 of the conduit 18. An electric wire 92 connects electrodes 90 and 91, and electric wire 93 leads away from electrode 91. Correspondingly, one electrode 94 is arranged on the conduit 18 between the valve 87 and the syringe, and one electrode 95 is arranged on the conduit 53 between the syringe and the valve 54. An electric wire 96 connects electrodes 94 and 95, and an electric wire 97 leads away from electrode 95. In order to prevent short-circuiting between the electrodes 90, 91 and 94, 95 the valve 87 has an insulating function in its closed position. A branch conduit 98 leads away from the conduit 18 and has a valve 99.

In operation of the embodiment of FIG. 5, the diluting liquid and blood sample displaced by the piston 33 through the conduit 18 passes the loop 83 before entering the chamber 82. In passing the legs 84 and 85 of the loop, the liquid will flush away air bubbles possibly adhering to the inner sides of the legs 84, 85, particularly the portions thereof serving as electrodes. At this stage the valve 87 is open and the valve 99 closed as are the valves 54 and 89. Due to the very small opening of the capillary 86, only a neglectible volume of the liquid will enter the chamber 82 through the capillary.

When the predetermined volume has entered the chamber 82, the valve 54 is opened to introduce air into the chamber 82 for mixing the blood sample with the diluting liquid. Thereupon the valve 54 is closed, the valve body of the turning valve 20 is brought to the position shown blocking conduit 18, the valve 87 is closed and the valve 99 is opened. The piston 33 is lowered to press the diluted sample through the capillary 86 and the leg 84 of the loop 83 into the conduit 18 from where it enters the conduit 98. In the conduit 98 there is a transparent portion having two light sensors 100 and 101 spaced therealong a distance 102 corresponding to a predetermined volume within the conduit 98. These sensors will sense a change in the refractive index of the liquid passing them. Since the conduit 18 will be filled with only clear diluting liquid after having displaced the volume of blood sample contained within the through channel 21 of the turning valve 20 through the conduit 18 and into the chamber 82, the liquid first passing the sensors will be the transparent volume of diluting liquid contained in the portion of the conduit 18 between the capillary 86 and the branching point between conduits 18 and 98. As soon as liquid having another refractive index, i.e. diluted blood sample, passes the first sensor, the blood cell counting starts, and as soon as the same change is indicated at the second sensor, the counting stops. The result obtained is the number of blood cells contained within the defined volume (typically 200–400 $\mu$l) between the sensors 100 and 101, and this number is divided by the predetermined volume to obtain the concentration in the sample. It is now easy to determine the concentration of blood cells in the original, undiluted blood sample by multiplying by the dilution factor.

What is claimed is:

1. A diluting and measuring device for particle counting, including metering means for metering a defined volume of a liquid sample containing particles, dosing means for dosing a defined volume of a diluting liquid for diluting said defined volume of said sample, and a dilution chamber, said dosing means including a cylinder having a first and a second end and a piston axially movable in said cylinder and having a first and a second piston side, characterized by first conduit means connecting said first end of said cylinder and said dilution chamber, said metering means being adapted to introduce said defined volume of said liquid sample in said first conduit means, whereby movement of said piston towards said first end causes displacement of said defined volume of said diluting liquid through said first conduit means to said dilution chamber, thereby bringing along said defined volume of said sample to be diluted by said diluting liquid in said dilution chamber;

said dilution chamber communicating with said second end of said cylinder, whereby movement of said piston towards said second end causes pressurizing of said dilution chamber to displace diluted sample from said dilution chamber through a particle counting means communicating with said dilution chamber.

2. A diluting and measuring device according to claim 1, characterized in that said particle counting means is located in a wall of said dilution chamber which is also a measuring chamber.

3. A diluting and measuring device according to claim 2, characterized in that said dilution chamber comprises said second end of said cylinder.

4. A diluting and measuring device according to claim 1, characterized in that said particle counting means is located in a wall of a separate measuring chamber communicating with said dilution chamber.

5. A diluting and measuring device according to claim 1, characterized in that said dilution chamber comprises said second end of said cylinder.

6. A diluting and measuring device according to claim 5, characterized in that said first conduit means describes a substantially vertical loop connected to said cylinder such that the interior of the cylinder on said second piston side communicates with said first conduit means through said particle counting means.

7. A diluting and measuring device according to claim 6, characterized in that said loop includes a first and a second leg joined in a position where said first conduit means is connected to said cylinder, that said first leg ascends towards said position and said second leg ascends from said position, and that at least one of said legs includes an electrically conducting portion constituting first electrode means electrically connected to liquid within said first conduit means.

8. A diluting and measuring device according to claim 7, characterized in that at least one second electrode means is provided being electrically connected to liquid within said cylinder on said second piston side.

9. A diluting and measuring device according to claim 8, characterized in that said second electrode means is constituted by an electrically conducting portion of at least one second conduit means.

10. A diluting and measuring device according to claim 1, characterized in that said piston is operable by means of a piston rod connected to said first piston side and extending through said first cylinder end, whereby movement of said piston towards said first end causes an increase in volume in said cylinder on said second piston side that is greater than the decrease in volume in said cylinder on said first piston side, said increase causing a lowered pressure in an air volume on said second piston side, said cylinder being provided with means for letting atmospheric air into said cylinder at its second end to equalize said lowered pressure.

11. A diluting and measuring device according to claim 10, characterized in that said means for letting atmospheric air into said cylinder opens in a lower portion of said dilution chamber located below a common liquid level of said defined volume of said diluting liquid and said defined volume of said sample contained within said dilution chamber.

* * * * *